(12) United States Patent
Yadollahi-Farsani et al.

(10) Patent No.: US 10,394,974 B2
(45) Date of Patent: Aug. 27, 2019

(54) GEOMETRY BASED METHOD FOR SIMULATING FLUID FLOW THROUGH HETEROGENEOUS POROUS MEDIA

(71) Applicants: Hooman Yadollahi-Farsani, Tempe, AZ (US); David Frakes, Scottsdale, AZ (US); Marcus Herrmann, Scottsdale, AZ (US)

(72) Inventors: Hooman Yadollahi-Farsani, Tempe, AZ (US); David Frakes, Scottsdale, AZ (US); Marcus Herrmann, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 374 days.

(21) Appl. No.: 15/277,381

(22) Filed: Sep. 27, 2016

(65) Prior Publication Data

US 2017/0098019 A1    Apr. 6, 2017

Related U.S. Application Data

(60) Provisional application No. 62/235,904, filed on Oct. 1, 2015.

(51) Int. Cl.
*G06F 17/50*    (2006.01)
*G01N 15/08*    (2006.01)
(Continued)

(52) U.S. Cl.
CPC ............ *G06F 17/5009* (2013.01); *A61F 2/07* (2013.01); *G01F 22/00* (2013.01); *G01N 15/08* (2013.01); *G06F 17/11* (2013.01)

(58) Field of Classification Search
CPC ....... G01V 99/005; E21B 43/00; E21B 49/00; G06F 17/5018; G06T 17/05; G01N 33/24; G01N 15/08
See application file for complete search history.

(56) References Cited

U.S. PATENT DOCUMENTS

| 5,146,086 A * | 9/1992 | De ........................ G01N 15/08 250/253 |
| 2008/0133186 A1* | 6/2008 | Li ....................... G06F 17/5018 703/2 |

(Continued)

OTHER PUBLICATIONS

Freeman, "Physicians Regional finding success with new treatment for aneurysms", Naples Daily News, Feb. 25, 2012, last accessed Aug. 29, 2016, <http://archive.naplesnews.com/business/physicians-regional-finding-success-with-new-treatment-for-aneurysms-ep-389894960-330860161.html>.

(Continued)

*Primary Examiner* — Kandasamy Thangavelu
(74) *Attorney, Agent, or Firm* — Norton Rose Fulbright US LLP

(57) ABSTRACT

A profile of porosities and permeabilities calculated from several sample volumes in a system can speed up computational fluid dynamics (CFDs). Heterogeneous fluid flow paths can be calculation intense, limiting the accuracy of fluid-path models. Further, allowing a user to define a number of sample volumes in a model system allows pre-calculation of porosities and permeabilities for use in Navier-Stokes formulas for modeling fluid flow and gives the user control over calculation time and accuracy. This is helpful, for example, in modeling endovascular interventions where fluid dynamics are determinative in the efficacy or method of treatment for various vascular disorders, such as aneurysms, and heart disease. This is also beneficial in other healthcare contexts, like blood filters, embolic gels, (Continued)

endografts, web devices, and atrial appendage occluders, among others. This disclosure is also relevant to fluid dynamics generally, such as in consumer products; and oil and gas exploration, recovery, and production.

21 Claims, 6 Drawing Sheets

(51) Int. Cl.
  *G01F 22/00* (2006.01)
  *G06F 17/11* (2006.01)
  *A61F 2/07* (2013.01)

(56) References Cited

U.S. PATENT DOCUMENTS

| | | | | |
|---|---|---|---|---|
| 2009/0216508 A1* | 8/2009 | Dale | ............ | E21B 43/00 703/10 |
| 2013/0116997 A1* | 5/2013 | Sun | ............ | G06F 17/5018 703/9 |
| 2013/0262028 A1* | 10/2013 | De Prisco | ............ | G01N 33/24 702/156 |
| 2014/0019053 A1* | 1/2014 | de Prisco | ............ | G06T 17/05 702/12 |
| 2014/0343858 A1* | 11/2014 | Crouse | ............ | E21B 49/00 702/13 |
| 2015/0066446 A1* | 3/2015 | Lin | ............ | E21B 43/00 703/2 |
| 2015/0338550 A1* | 11/2015 | Wadsley | ............ | E21B 43/00 703/2 |
| 2016/0025895 A1* | 1/2016 | Ziauddin | ............ | G01V 99/005 702/11 |

OTHER PUBLICATIONS

Koponen et al., "Permeability and effective porosity of porous media", Physical Review E, Sep. 1997, 56(3):3319-25.
Spencer, Brain Aneurysms., Brain Aneurysm Web Quest, Longwood Blogs, Feb. 2012 <http://blogs.longwood.edu/bio207webquest/>.

\* cited by examiner

GEOMETRY BASED METHOD FOR SIMULATING FLUID FLOW THROUGH HETEROGENEOUS POROUS MEDIA

CROSS-REFERENCE

This application claims the benefit of U.S. Provisional Application No. 62/235,904 filed Oct. 1, 2015, the entire contents of which is incorporated herein by reference.

The invention was made with government support under Grant No. 1151232 awarded by the National Science Foundation. The government has certain rights in the invention.

BACKGROUND OF THE INVENTION

Field of the Invention

The invention generally concerns computational fluid dynamics. More specifically, the invention concerns simulating fluid flow through heterogeneous porous media, such as in endovascular systems, fluid filtration, oil and gas recovery, etc.

Description of Related Art

In computational fluid dynamics (CFD), modeling heterogeneous fluid paths is computationally intensive and simplifications of the heterogeneous fluid path aimed at reducing computational burdens impact the accuracy of CFD modeling. Currently, there is a significant drawback associated with the homogeneous porous medium assumption implemented in literature because of the change in porosity throughout the domain. In other words, the fluid capability to flow in a porous medium is dependent on the resistance of the seepage path. For example, at some regions the porosity is higher which leads to a lower resistance. This can change in the other regions requiring a heterogeneous porous medium for more accurate modeling.

One area where heterogeneous fluid path modeling is particularly helpful is in diagnostic and evaluative modeling of endovascular systems, e.g., modeling the vascular system of patients at risk for or who have suffered from an aneurysm, stroke, cardiovascular disease, or heart disease. Endovascular systems are indicated herein as illustrative embodiments; however, it should be understood that the disclosed CFDs are relevant to many health care applications including endovascular devices, blood flow in the eye's choriocapillaris, fluid flow through fibrous materials used in healthcare and consumer products applications (e.g., napkins, diapers, stents, wire meshes, and/or the like). The disclosed CFDs are also relevant to other industries, including, but not limited to, oil and gas industrial applications. For example, the disclosed CFDs may be used to ascertain or estimate fluid flow through rocks, carbon sequestration, and/or gas recovery. Similarly, the present CFDs may be applied to fluidic filtration technologies in nearly any field, including water filtration, chemical filtration, and/or the like.

Interventions for vascular disorders often include introducing permanent or semi-permanent structures into the vascular system, e.g., endovascular devices. For example, patients at risk for an aneurysm develop an aneurysm sac where the vascular wall may eventually rupture. FIG. 1A illustrates an aneurysm sac 110. One mitigating procedure for the development of an aneurysm sac is shown in FIG. 1B, where platinum coils 120 deployed within an aneurysm sac 110. These coils promote thrombosis within the sac, and over time, the aneurysmal neck 130 will be occluded, preventing further blood flow to the aneurysm sac and reducing or eliminating the risk of rupture. Modeling the environment and coil prior to surgery assists with evaluation of outcome and procedure details, e.g., coil formation and geometry. Modeling aneurysm sacs and coils in vascular system is calculation intensive, which limits accuracy, the number of variables, and the number scenarios that can be efficiently evaluated preoperatively. Thus, there is a need for enhancements in hemodynamic modeling methods and systems to provide greater flexibility, accuracy, and speed in dynamic fluid flow modeling. Stents and pipeline embolization devices (PEDs), illustrated as 140 in FIG. 1C and as 150 in FIG. 1D, respectively, for maintaining open vasculature also benefit from hemodynamic modeling to aid in predicting outcome and efficacy of intervention.

SUMMARY OF THE INVENTION

CFDs of heterogeneous fluid flow paths can be extremely calculation intense which limits the accuracy of fluid-path models. CFD modeling may be performed more quickly and accurately with profiles of porosity and permeability where the profiles are based on several sample volumes within a model system. In some embodiments of the present disclosure, a porosity and permeability profile may be calculated separately from the CFD solver and serve as inputs to the CFD solver to facilitate faster and more accurate fluid dynamic models.

The heterogeneity assumption is often associated with complexities in deriving spatial dependent porosity equations. Moreover, the permeability of heterogeneous fluid flow paths needs to be defined as a position dependent quantity. A 3D map or profile of porosity and permeability for the whole domain facilitates accurate results in a relatively short amount of time. This approach may substantially decrease the time needed to simulate the fluid dynamics of a model system. To use an illustration of the presently disclosed CFDs in a healthcare application, doctors who are willing to simulate the hemodynamics in a part of the body with a deployed device may be assisted by the solutions provided in the present disclosure.

In some embodiments, a sample volume or filter is defined within a 3D system that is to be modeled. The volume of the sample volume is calculated. A volume for the portion of any 3D object within the sample volume is also calculated. These volumes are then used to calculate a porosity for the sample volume. Similarly, the surface area of the portion of any 3D objects within the sample volume is also calculated. The calculated volumes and surface area are used to calculate a permeability for the sample volume. These calculations are repeated for several sample volumes to create map or profile of the porosities and permeabilities in the 3D system that is being modeled. In some embodiments, the map of porosities and permeabilities may be used in a CFD solver to simulate fluid flow through the 3D system. In some embodiments, the 3D system is a fluid flow-path. In some embodiments, the 3D system is a portion of an endovascular system. In some embodiments, the portion of the endovascular system includes an obstruction where the obstruction may be an endovascular device (e.g., coil, PED, or stent), a blood filter, embolic gel, endograft, web device, or atrial appendage occluder. In some embodiments, the volume of the portion of any 3D object within the sample volume is calculated using the divergence theorem based on the surface area of the portion of the object within the sample volume.

Some embodiments are a computer-implemented method comprising receiving a digital file comprising geometric data defining a three-dimensional model of an object configured to be disposed in a fluid flow-path; defining a plurality of sample volume representations of a portion of the fluid flow-path; determining an orientation for the model relating to the sample volumes; for each of the sample volumes within which a portion of the model is disposed: calculating a first volume based, at least in part, on the volume of the sample volume; calculating a second volume based at least partially on the volume of the portion of the model; calculating a first porosity based at least partially on the first volume and the second volume; and generating a porosity profile based on the calculated porosities of the sample volumes.

Some embodiments further comprise calculating an area of the three dimensional object that is in the sample volume; calculating a permeability based, at least in part, on the area and the first porosity; and generating a profile of permeabilities based on the calculated permeabilities of the sample volumes for each of the samples volumes within which a portion of the model is disposed. Some embodiments further comprise simulating a fluid flow around the model based, at least in part, on the first and second porosities.

Some embodiments comprise determining a set of geometric samples that consist of points, lines, vertices, triangles, or polygons that intersect the boundaries of the sample volume for each of the sample volumes within which a portion of the model is disposed. Some embodiments comprise calculating a second area based on the set of geometric samples that intersect the boundaries of the sample volume for each of the sample volumes within which a portion of the model is disposed. Some embodiments comprise calculating the permeability based, at least in part, on the third area for each of the sample volumes within which a portion of the model is disposed.

Some embodiments comprise determining the set of geometric samples that intersect the boundaries of the sample volume for each of the sample volumes within which a portion of the model is disposed comprises tessellating the geometric samples between the geometric representation and the first sample volume boundaries. In some embodiments, the second volume for each of the sample volumes within which a portion of the model is disposed is calculated using a divergence of the first area. In some embodiments, the geometric data defining a three-dimensional model of an object configured to be disposed in a fluid flow-path is defined by a Stereo Lithography (STL) file. In some embodiments, the sample volume for each of the sample volumes within which a portion of the model is disposed is an axis-aligned bounding box (AABB).

Some embodiments are a computer program product, comprising a non-transitory computer readable medium comprising code for performing the disclosed methods. Some embodiments are an apparatus, comprising a memory; and a processor coupled to the memory, wherein the processor is configured to execute the steps the disclosed methods.

Some embodiments comprise receiving a geometric data defining a three-dimensional model of an object configured to be disposed in a fluid flow-path. Some embodiments comprise calculating a sample volume where at least a portion of the geometric data is within the sample volume. Some embodiments comprise calculating a first volume based on a volume of the sample volume; determining a first portion of the geometric data that is entirely within the sample volume. Some embodiments comprise determining a second portion of the geometric data that is partially within the sample volume. Some embodiments comprise calculating a set of intersection points of the second portion of the geometric data and the sample volume. Some embodiments comprise tessellating the second portion of the geometric data that is bounded within the sample volume and the second portion of the geometric data. Some embodiments comprise tessellating the set of intersection points of the second portion. Some embodiments comprise calculating a first area defined by the first portion of the geometric data. Some embodiments comprise calculating a second area defined by the second portion of the geometric data. Some embodiments comprise calculating a third area defined by the set of intersection points. Some embodiments comprise calculating a second volume based on the first area. Some embodiments comprise calculating a third volume based on the second area. Some embodiments comprise calculating a fourth volume based on the third area. Some embodiments comprise calculating a mesh volume based on the second, third and fourth volumes. Some embodiments comprise calculating a porosity based on the volume of the sample volume and the mesh volume. Some embodiments comprise calculating a permeability based, at least in part, on the first area, the second area, and the porosity. Some embodiments may additionally include calculating permeability based, at least in part, on the third area. Some embodiments comprise simulating a fluid flow around the model based on the permeability and the porosity.

In some embodiments, the geometric data defines the model object with at least one of points, lines, vertices, triangles, or polygons. In some embodiments calculating of at least one of the second volume, third volume, and fourth volume is calculated using the divergence theorem.

The term "coupled" is defined as connected, although not necessarily directly, and not necessarily mechanically.

The terms "a" and "an" are defined as one or more unless this disclosure explicitly requires otherwise.

The term "substantially" is defined as being largely but not necessarily wholly what is specified (and include wholly what is specified) as understood by one of ordinary skill in the art. In any disclosed embodiment, the term "substantially" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, the methods and systems of the present invention that "comprises," "has," "includes" or "contains" one or more elements possesses those one or more elements, but is not limited to possessing only those one or more elements. Likewise, an element of a method or system of the present invention that "comprises," "has," "includes," or "contains" one or more features possesses those one or more features, but is not limited to possessing only those one or more features.

Furthermore, a structure that is capable of performing a function or that is configured in a certain way is capable or configured in at least that way, but may also be capable or configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any method or system of the present invention can consist of or consist essentially of—rather than comprise/ include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION OF THE INVENTION

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

In the following description, numerous specific details are provided to give a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1A:
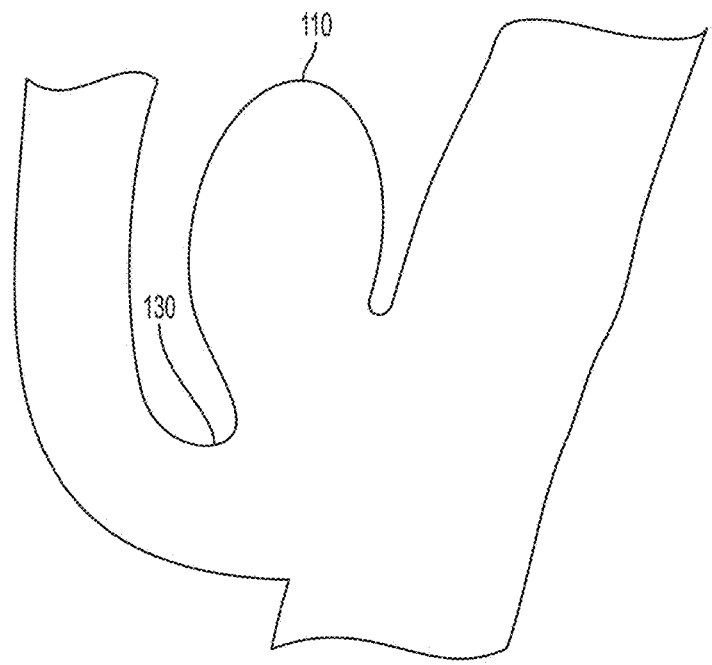
FIGS. 1A-D illustrate vascular environments and applications, such as an aneurysm sac, aneurysm treatment coil, stent and pipeline embolization device (PED) where fluid flow modeling and the present methods and apparatuses may be employed.
Figure 1B:
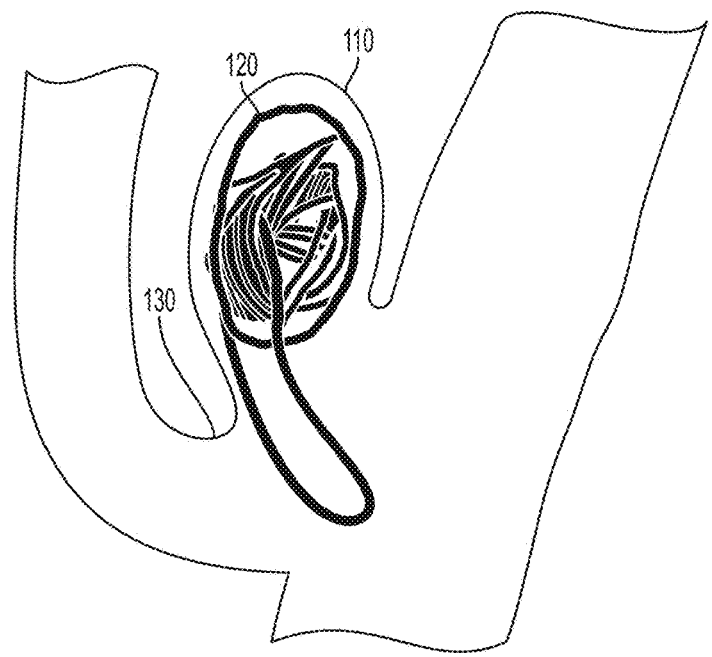
Figure 1C:
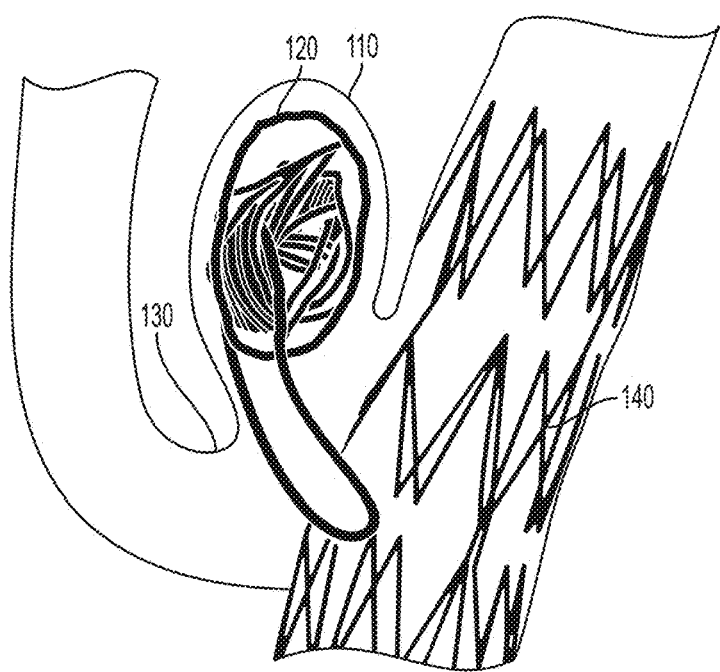
Figure 1D:
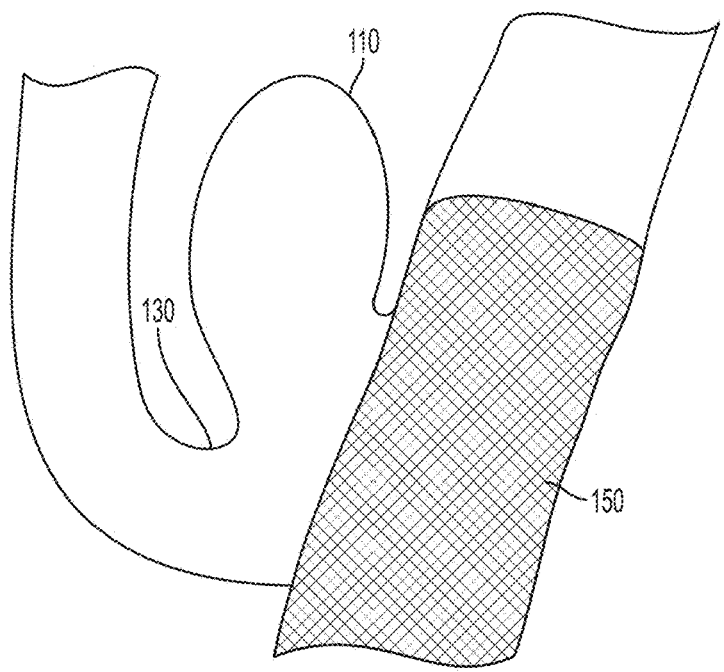

In CFDs, modeling heterogeneous fluid paths is computationally intensive and oversimplifications of the heterogeneous fluid path that reduce computational burdens impact the accuracy of CFD modeling. Some embodiments of the present methods and apparatuses facilitate modeling hemodynamics of vascular disorders such as the aneurysm sac 110 illustrated in FIG. 1A. Some embodiments may be used to facilitate modeling fluid flow through or around endovascular devices such as the coil 120 in FIG. 1B, the stent 140 in FIG. 1C, or the PED 150 in FIG. 1D.

Figure 2:
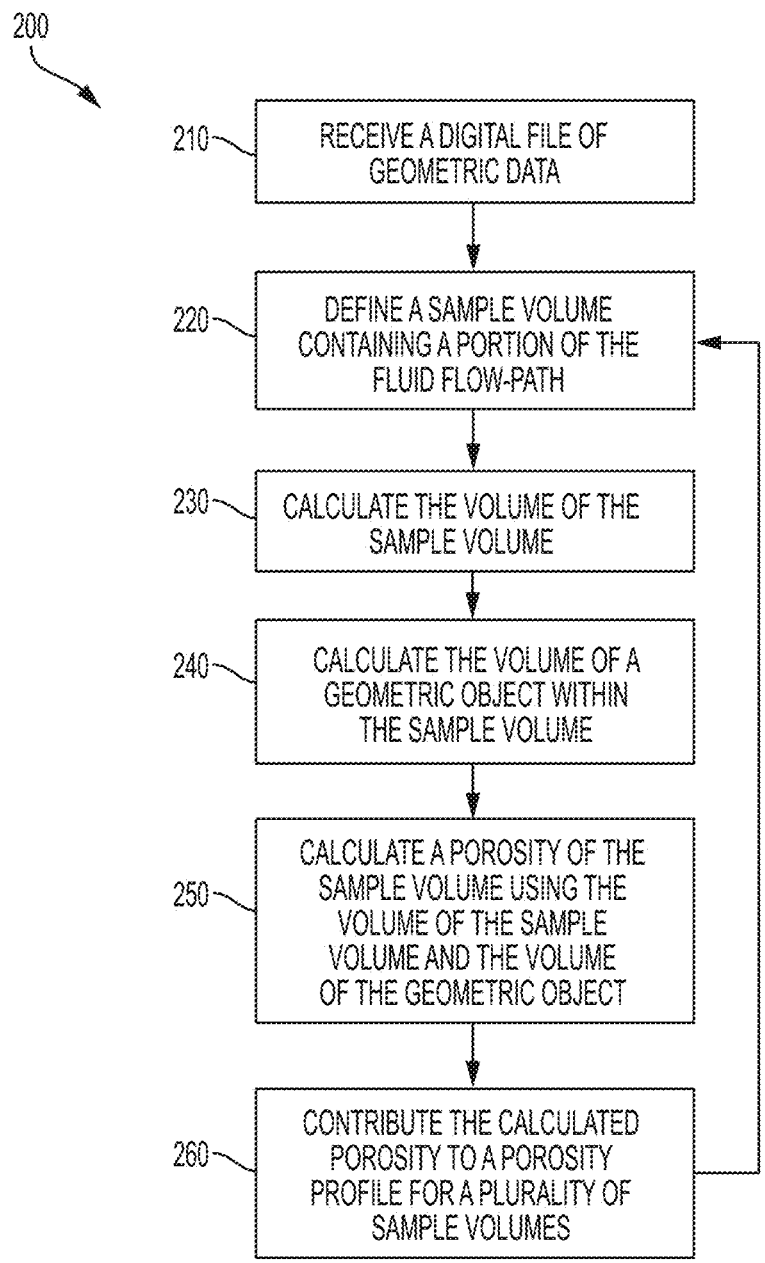
FIG. 2 is an illustrative process flow of one embodiment of the present methods and apparatuses for calculating a porosity of one or a plurality of sample volumes.

Some embodiment of the present methods and apparatuses are illustrated in FIG. 2. In some embodiments, a digital file comprising geometric data defining a three-dimensional model of an object configured to be disposed in a fluid flow-path is received at step 210. At step 220, a plurality of sample volumes are defined that represent at least a portion of the fluid flow-path. In some embodiments, the orientation for the model relating to the sample volumes is determined. In some embodiments, the sample volume for each of the sample volumes within which a portion of the model is disposed is an AABB. In step 230 a first volume based, at least in part, on the volume of the sample volume is calculated. In step 240, a second volume based at least partially on the volume of the portion of the model is calculated (e.g., the volume illustrated in the calculation of step 530 of the embodiment in FIG. 5). In step 250, a first porosity based at least partially on the first volume and the second volume is calculated. In step 260 the porosity of the sample volume is contributed to a porosity profile and steps 220-250 are repeated. In some embodiments, steps 220-260 are repeated until a sample volume has been calculated in every space of the model system. In some embodiments, the porosity profile comprises an average or weighted average. In some embodiments, the porosity profile is a matrix of porosity values for several sample volumes. The calculations illustrated in FIG. 2 may be used to also calculate a permeability profile, as illustrated in FIG. 3.

Figure 3:
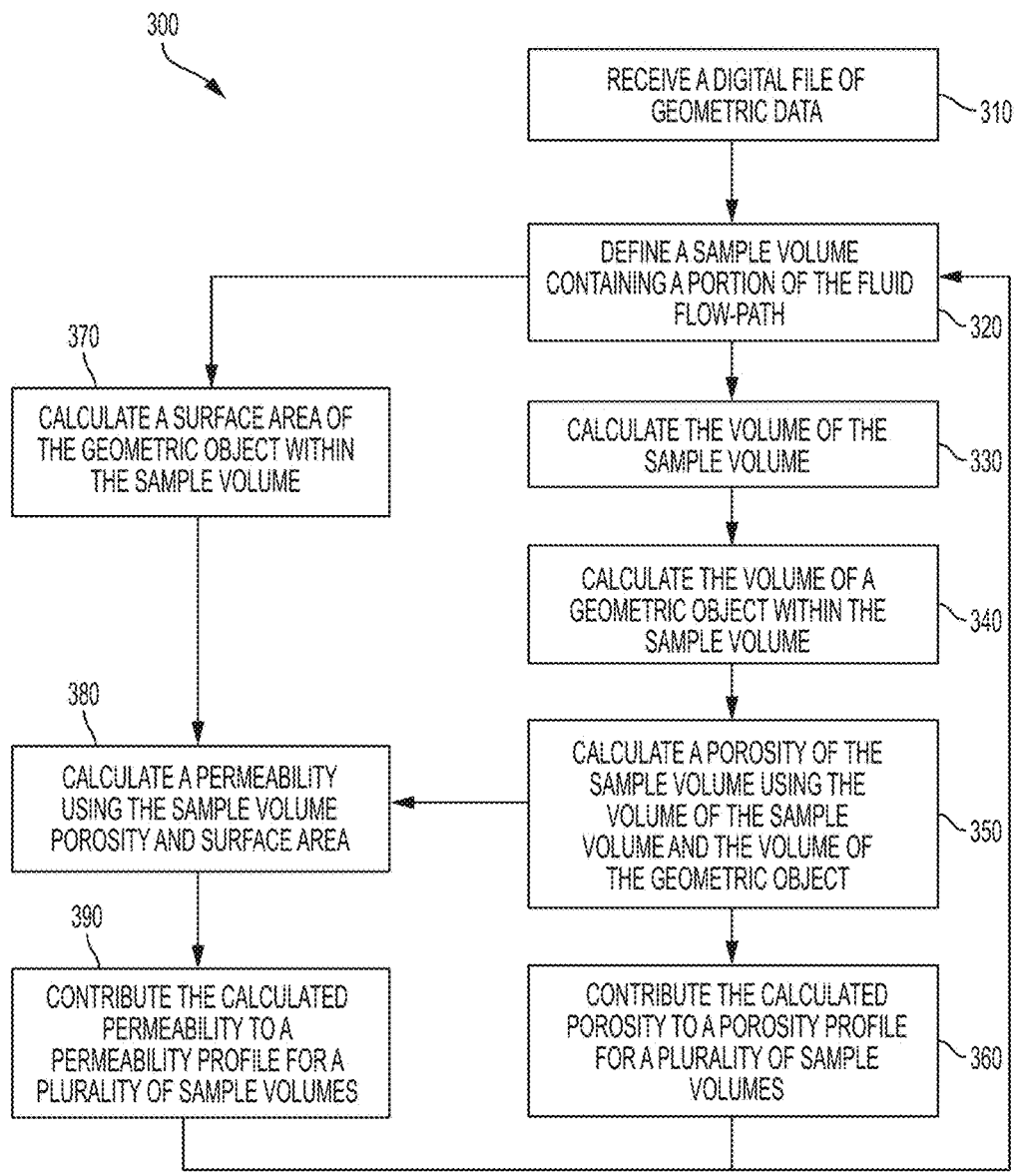
FIG. 3 is an illustrative process flow of one embodiment of the present methods and apparatuses for calculating a porosity and a permeability of one or a plurality of sample volumes.

FIG. 3 illustrates calculating both the porosity profile and a permeability profile for a system that, in some embodiments, is to be used in a CFD solver. The sample volume from step 320 is used to define and calculate a surface area of the geometric object within the sample volume in step 370. The surface area from calculation 370 and the porosity from step 350 may then be used to calculate a permeability in step 380. In step 390 the permeability of the sample volume is contributed to a permeability profile and steps 320-390 are repeated. In some embodiments, steps 320-390 are repeated until a sample volume has been calculated in every space of the model system. In some embodiments, the permeability profile comprises an average or weighted average. In some embodiments, the permeability profile is a matrix of permeability values for several sample volumes. The porosity and permeability profiles are then used in a CFD solver to simulate fluid flow in a model system.

Figure 4:
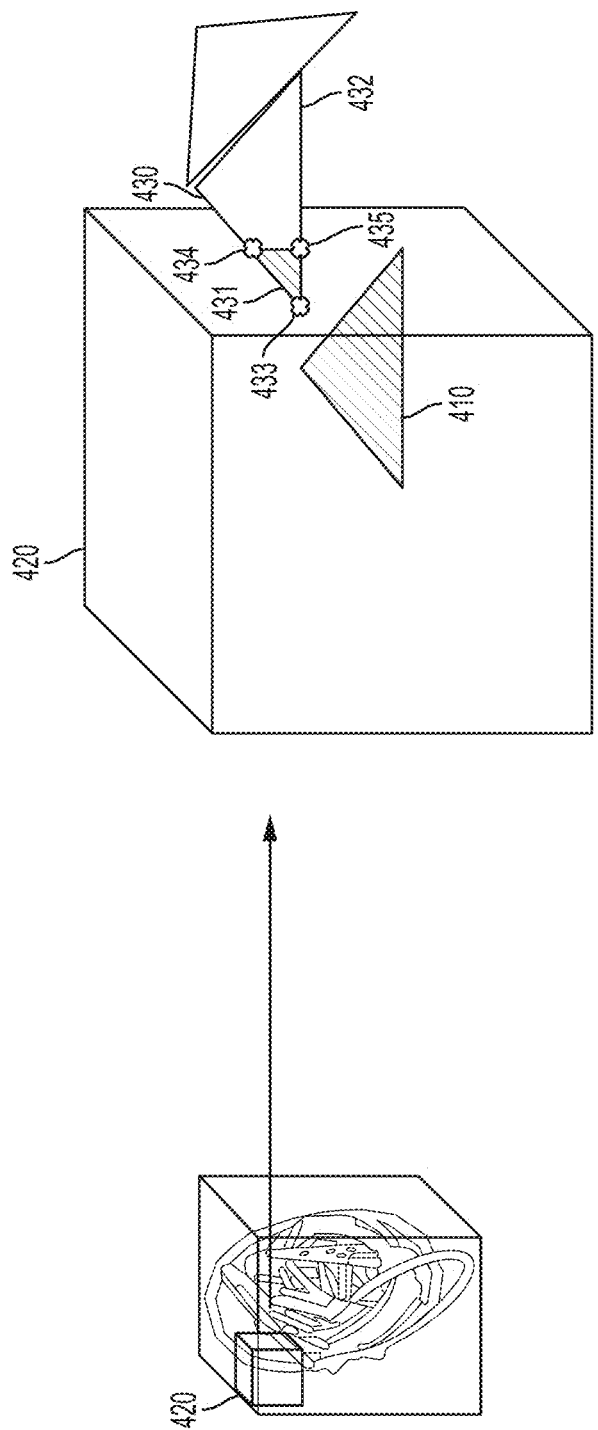
FIG. 4 is a conceptual depiction of one embodiment of the sample volumes and model volume.
Figure 5:
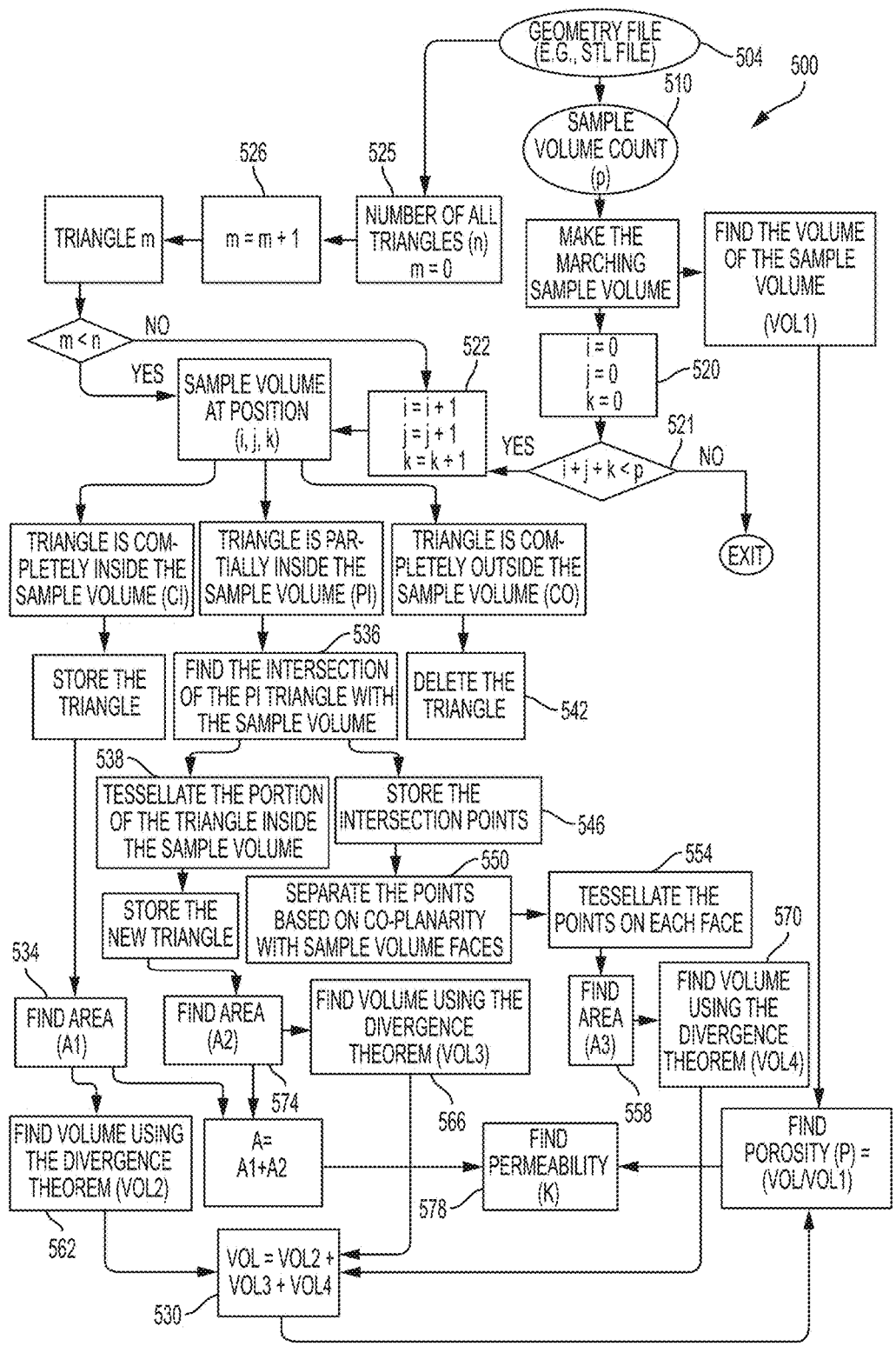
FIG. 5 is a flow diagram illustrating one embodiment of the present methods and apparatuses to calculate a porosity and permeability profile to be used in a CFD solver.

In some embodiments, the surface areas calculated in step 370 of FIG. 3 may also include calculating surface areas for geometries that intersect the sample volume or that are co-planar with the sample volume (e.g., the intersection points found at step 536 of FIG. 5). FIG. 4 illustrates three geometric triangles from the geometric data received in steps 210 and 310 of FIGS. 2 and 3, respectively. Triangle 410 lies entirely within sample volume 420 and in some embodiments forms a second surface area (e.g., area A1 calculated in step 534 of the embodiment illustrated in FIG. 5). In some embodiments, the second surface area is also part of the basis for the surface area calculated in step 370 of FIG. 3. In some embodiments, the surface area that is eventually used in calculating the permeability may also include the surface area of triangle 430 that lies within the sample volume 431. In some embodiments, triangle 431 is calculated by tessellating between the point 433 of the cutoff triangle 430 and the two points 434 and 435 that are on the facial plane of the sample volume (e.g., step 538 in the embodiment illustrated in FIG. 5). In some embodiments, the portion of the triangle outside the sample volume 420 is ignored or deleted for the purposes of calculating the permeability of the sample volume (e.g., step 542 in the embodiment illustrated in FIG. 5). In some embodiments, the points 434 and 435 of the cut-off triangles, e.g., 430, that lie on the face of the sample volume are tessellated with other points on the face of the sample volume from other truncated geometric shapes to define a set of triangles or other geometries on the face of the sample volume (e.g., steps 546, 550, and 554 in the embodiment illustrated in FIG. 5). These geometries may then be used to calculate a third surface area (e.g., step 558 in the embodiment illustrated in FIG. 5). In some embodiments, this third surface area is also part of the surface area calculated in step 370 of FIG. 3.

In some embodiments, the volume of the three-dimensional object represented by the geometric data is calculated using a divergence of the surface area (e.g., steps 562, 566, and 570 in FIG. 5). Any combination of the first, second, and third surface areas described above may be used to calculate a volume by divergence (e.g., the areas calculated in steps 534, 558, and/or 574 in FIG. 5).

In some embodiments of the present methods and apparatuses, the geometric data defining the three-dimensional model of an object configured to be disposed in the fluid-flow path is defined by a Stereo Lithography (STL) file (e.g., the file loaded in at step 504 of FIG. 5). The present disclosure is not limited to the use of an STL file. Various file formats are available that are compatible with the present disclosure, e.g., files that define the geometry of an object using a surface mesh.

Some embodiments of the present methods and apparatus are implemented on a computer. In some embodiments, a mathematical software tool such as Matlab or Mathematica might be used. Some embodiments comprise a computer program product with a non-transitory computer readable medium comprising code for calculating a porosity or a permeability for a sample volume. Some embodiments comprise an apparatus with a memory and a processor coupled to the memory, where the processor is configured to calculate a porosity or a permeability for a sample volume. Some embodiments are configured to use a porosity profile and/or a permeability profile to model fluid flow in a fluid-path.

The steps illustrated in FIGS. 2 and 3 may also proceed in different orders. For example, FIG. 5 illustrates a process flow for one embodiment of the present methods and apparatuses. In some embodiments, and as illustrated in FIG. 5, the filter count in step 510 is user programmable. Some embodiments also comprise a plurality of counters, e.g., steps 520, 521, 522, 525, and 526 for tracking the progression of filter calculations to march through the volume of the model system.

In some embodiments, the Navier-Stokes equations are used to simulate fluid dynamics. Some embodiments of the present methods simulate a porous medium where:

$$\rho\left(\frac{\partial u}{\partial t} + u \cdot \nabla u\right) = -\nabla p + \mu \nabla^2 u + S$$

$$S = -\frac{\mu}{k} u$$

In some embodiments, ρ is density of fluid, u is velocity field, μ is dynamic viscosity, p is pressure field and S is the source term associated with the implementation of the porous medium. Permeability (k) is defined using the Kozeny-Carman equation as:

$$k = \frac{\phi^3}{cA^2}$$

In some embodiments, ϕ is the porosity, A is the interstitial surface area, and c is the shape factor. The embodiment illustrated in FIG. 5 provides an example of a permeability (k) calculated in the system 500 at step 578.

The advantage of this method is the significant reduction in the number of the mesh elements needed to simulate the fluid dynamics. This can reduce the computational costs considerably. After generating the 3D map (i.e., profile) of porosity and permeability, a CFD solver is used to simulate the fluid dynamics.

The above specification and examples provide a complete description of the structure and use of an exemplary embodiment. Although certain embodiments have been described above with a certain degree of particularity, or with reference to one or more individual embodiments, those skilled in the art could make numerous alterations to the disclosed embodiments without departing from the scope of this invention. As such, the illustrative embodiment of the present computational fluid dynamics is not intended to be limited to the particular forms disclosed. Rather, they include all modifications and alternatives falling within the scope of the claims, and embodiments other than the one shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

What is claimed is:

1. A computer-implemented method comprising:
   receiving a digital file comprising geometric data defining a three-dimensional model of an object disposed in a fluid-flow path of an endovascular system;
   defining geometric representations of a plurality of sample volumes of a portion of the fluid-flow path;
   determining an orientation for the model relating to the sample volumes;
   for each of the sample volumes within which a portion of the model is disposed:
   calculating a first volume based, at least in part, on the volume of the sample volume;
   calculating a second volume based at least partially on the volume of the portion of the model disposed in the sample volume;
   calculating a porosity based at least partially on the first volume and the second volume; and repeating the calculating the first volume, calculating the second volume, calculating a porosity for each of the sample volumes within which a portion of the model is disposed;

generating a porosity profile based on the calculated porosities of the sample volumes;

simulating a fluid-flow in a computational model of the fluid-flow path of the endovascular system containing the three-dimensional model of the object using the generated porosity profile;

evaluating the outcome of a procedure to implant the object in the endovascular system and evaluating the efficacy and geometry of the object for maintaining open vasculature, using the simulation results.

2. The method of claim 1, further comprising for each of the samples volumes within which a portion of the model is disposed:

calculating a first volume based, at least in part, on the volume of the sample volume;

calculating a first surface area of the portion of the model disposed in the sample volume;

calculating a permeability based, at least in part, on the first surface area and the porosity;

repeating the calculating the first volume, calculating the first surface area and calculating a permeability for each of the sample volumes within which a portion of the model is disposed;

generating a profile of permeabilities based on the calculated permeabilities of the sample volumes;

simulating a fluid-flow in a computational model of the fluid-flow path of the endovascular system containing the three-dimensional model of the object using the generating profile of permeabilities;

evaluating the outcome of a procedure to implant the object in the endovascular system and evaluating the efficacy and geometry of the object for maintaining opening vasculature, using the simulation results.

3. The method of claim 2, wherein the second volume for each of the sample volumes within which a portion of the model is disposed is calculated using a divergence of the first surface area.

4. The method of claim 1, further comprising, for each of the sample volumes within which a portion of the model is disposed:

determining a set of geometric samples that consist of at least one of points, lines, vertices, triangles, or polygons that intersect a first boundary of the sample volume;

calculating a second surface area based on the set of geometric samples that intersect the first boundary of the sample volume;

where calculating the permeability is based, at least in part, on the second surface area.

5. The method of claim 4, wherein determining the set of geometric samples that intersect a first boundary of the sample volume for each of the sample volumes within which a portion of the model is disposed comprises tessellating the geometric samples between a geometric representation and the first boundary of the sample volume.

6. The method of claim 1, wherein the geometric data defining a three-dimensional model of an object disposed in a fluid-flow path is defined by a Stereo Lithography (STL) file.

7. The method of claim 1, wherein the sample volume for each of the sample volumes within which a portion of the model is disposed is an axis-aligned bounding box (AABB).

8. An apparatus, comprising:
a memory; and
a processor coupled to the memory, wherein the processor is configured to execute the steps of:
receiving a digital file comprising geometric data defining a three-dimensional model of an object disposed in a fluid-flow path of an endovascular system;
defining geometric representations of a plurality of sample volumes of a portion of the fluid-flow path;
determining an orientation for the model relating to the sample volumes;
for each of the sample volumes within which a portion of the model is disposed:
calculating a first volume based, at least in part, on the volume of the sample volume;
calculating a second volume based at least partially on the volume of the portion of the model disposed in the sample volume;
calculating a porosity based at least partially on the first volume and the second volume; and
repeating the calculating the first volume, calculating the second volume, calculating a porosity for each of the sample volumes within which a portion of the model is disposed;
generating a porosity profile based on the calculated porosities of the sample volumes;
simulating a fluid-flow in a computational model of the fluid-flow path of the endovascular system containing the three-dimensional model of the object using the generated porosity profile; and
evaluating the outcome of a procedure to implant the object in the endovascular system and evaluating the efficacy and geometry of the object for maintaining open vasculature, using the simulating results.

9. The apparatus of claim 8, where the processor is further configured, for each of the sample volumes within which a portion of the model is disposed, to execute the steps of:

calculating a first volume based, at least in part, on the volume of the sample volume;

calculating a first surface area of the portion of the model disposed in the sample volume;

calculating a permeability based, at least in part, on the first surface area and the porosity;

repeating the calculating the first volume, calculating the first surface area and calculating a permeability for each of the sample volumes within which a portion of the model is disposed;

generating a profile of permeabilities based on the calculated permeabilities of the sample volumes;

simulating a fluid-flow in a computational model of the fluid-flow path of the endovascular system containing the three-dimensional model of the object using the generated profile of permeabilities; and evaluating the outcome of a procedure to implant the object in the endovascular system and evaluating the efficacy and geometry of the object for maintaining open vasculature, using the simulating results.

10. The apparatus of claim 9, wherein the processor is further configured to execute the step of calculating the second volume using a divergence of the first surface area.

11. The apparatus of claim 8, where the processor is further configured to execute, for each of the sample volumes within which a portion of the model is disposed, the step of:

determining a set of geometric samples that consist of at least one of points, lines, vertices, triangles, or polygons that intersect a first boundary of the sample volume;

calculating a second surface area based on the set of geometric samples that intersect the first boundary of the sample volume;

where calculating the permeability is based, at least in part, on the second surface area.

12. The apparatus of claim 11, wherein the processor is further configured to execute the step of determining the set of geometric samples that intersect a first boundary of the sample volume for each of the sample volumes within which a portion of the model is disposed comprises tessellating the geometric samples between a geometric representation and the first boundary of the sample volume.

13. The apparatus of claim 8, wherein the geometric data defining a three-dimensional model of an object configured to be disposed in a fluid flow-path is defined by a Stereo Lithography (STL) file.

14. The apparatus of claim 8, wherein the sample volume for each of the sample volumes within which a portion of the model is disposed is an axis-aligned bounding box (AABB).

15. A method comprising:
receiving a geometric data defining a three-dimensional model of an object disposed in a fluid-flow path of an endovascular system;
defining geometric representations of a plurality of sample volumes of a portion of the fluid-flow path;
for each of the sample volumes within which a portion of the model is disposed:
calculating a first volume based on a volume of the sample volume;
determining a first portion of the model that is entirely within the sample volume;
determining a second portion of the model that is partially within the sample volume;
calculating a set of intersection points of the second portion of the model and the sample volume;
tessellating the second portion of the model that is bounded within the sample volume and the second portion of the model;
tessellating the set of intersection points of the second portion;
calculating a first surface area defined by the first portion of the model;
calculating a second surface area defined by the second portion of the model;
calculating a third surface area defined by the set of intersection points;
calculating a second volume based on the first surface area;
calculating a third volume based on the second surface area;
calculating a fourth volume based on the third surface area;
calculating a mesh volume based on the second, third and fourth volumes;
calculating a porosity based on the volume of the sample volume and the mesh volume;
repeating the steps from calculating a first volume until calculating a porosity for each of the sample volumes within which a portion of the model is disposed;
generating a porosity profile based on the calculating porosities of the sample volumes;
simulating a fluid-flow in a computational model of the fluid-flow path of the endovascular system containing the three-dimensional model of the object using the generated porosity profile;
evaluating the outcome of a procedure to implant the object in the endovascular system and evaluating the efficacy and geometry of the object for maintaining open vasculature, using the simulation results.

16. The method of claim 15 further comprising for each of the sample volumes within which a portion of the model is disposed:
calculating a first volume based, at least in part, on the volume of the sample volume;
calculating a permeability based, at least in part, on the first surface area, the second surface area, and the porosity;
repeating the calculating the first volume, and calculating a permeability for each of the sample volumes within which a portion of the model is disposed;
generating a profile of permeabilities based on the calculated permeabilties of the sample volumes.

17. The method of claim 16 further comprising:
simulating a fluid-flow in a computational model of the fluid-flow path of the endovascular system containing the three-dimensional model of the object using the generated a porosity profile and the generated profile of permeabilities;
evaluating the outcome of a procedure to implant the object in the endovascular system and evaluating the efficacy and geometry of the object for maintaining open vasculature, using the simulation results.

18. The method of claim 15 wherein the geometric data defines the model object with at least one of points, lines, vertices, triangles, or polygons.

19. The method of claim 15 wherein the calculating of at least one of the second volume, third volume, and fourth volume is calculated using the divergence theorem.

20. The method of claim 15 wherein the geometric data of the model object is defined by a Stereo Lithography (STL) file.

21. The method of claim 15 wherein the sample volume is an axis-aligned bounding box (AABB).

* * * * *